US012660547B2

(12) United States Patent
Sasaki

(10) Patent No.: US 12,660,547 B2
(45) **Date of Patent: *Jun. 16, 2026**

(54) SUBSTRATE TREATING METHOD

(71) Applicant: SCREEN Holdings Co., Ltd., Kyoto (JP)

(72) Inventor: Yuta Sasaki, Kyoto (JP)

(73) Assignee: SCREEN Holdings Co., Ltd. (JP)

( * ) Notice: Subject to any disclaimer, the term of this patent is extended or adjusted under 35 U.S.C. 154(b) by 220 days.

This patent is subject to a terminal disclaimer.

(21) Appl. No.: 18/423,170

(22) Filed: Jan. 25, 2024

(65) Prior Publication Data

US 2024/0162033 A1 May 16, 2024

Related U.S. Application Data

(63) Continuation of application No. 16/910,116, filed on Jun. 24, 2020, now abandoned.

(30) Foreign Application Priority Data

Jun. 28, 2019 (JP) ................................ 2019-120655

(51) Int. Cl.

| | |
|---|---|
| ***H10P 72/00*** | (2026.01) |
| ***C07C 251/32*** | (2006.01) |
| ***C07C 251/44*** | (2006.01) |
| ***C11D 3/43*** | (2006.01) |
| ***C11D 7/32*** | (2006.01) |
| ***H10P 70/00*** | (2026.01) |

(52) U.S. Cl.

CPC ........ *H10P 72/0408* (2026.01); *C07C 251/32* (2013.01); *C11D 7/3209* (2013.01); *H10P 70/20* (2026.01); *C07C 251/44* (2013.01); *C11D 3/43* (2013.01); *C11D 7/32* (2013.01)

(58) Field of Classification Search

CPC .................................................. H10P 72/0408

See application file for complete search history.

(56) References Cited

U.S. PATENT DOCUMENTS

| | | | |
|---|---|---|---|
| 4,775,449 | A | 10/1988 | Dumas |
| 5,451,701 | A | 9/1995 | Zajacek |
| 2015/0155159 | A1 | 6/2015 | Igarashi et al. |
| 2017/0040154 | A1 * | 2/2017 | Kagawa .................. H10P 70/23 |
| 2017/0062244 | A1 * | 3/2017 | Sato .................... H10P 72/0414 |
| 2017/0345683 | A1 * | 11/2017 | Sasaki ................. H10P 72/0406 |
| 2018/0182646 | A1 | 6/2018 | Sasaki et al. |
| 2019/0096704 | A1 | 3/2019 | Sasaki et al. |
| 2020/0263087 | A1 | 8/2020 | Lim et al. |
| 2021/0157242 | A1 | 5/2021 | Wen et al. |

FOREIGN PATENT DOCUMENTS

| | | | |
|---|---|---|---|
| EP | 00962140 | A1 | 12/1999 |
| JP | S63-215603 | A | 9/1988 |
| JP | H03-074308 | A | 3/1991 |
| JP | 2000-044412 | A | 2/2000 |
| JP | 2012-243869 | A | 12/2012 |
| JP | 2015-106645 | A | 6/2015 |
| JP | 2017-076817 | A | 4/2017 |
| JP | 2018-107426 | A | 7/2018 |
| JP | 2019-062004 | A | 4/2019 |
| TW | 201734181 | A | 10/2017 |
| WO | WO 2019/024892 | A1 | 2/2019 |

* cited by examiner

*Primary Examiner* — Kaj K Olsen
*Assistant Examiner* — Richard Z. Zhang
(74) *Attorney, Agent, or Firm* — OSTROLENK FABER LLP

(57) ABSTRACT

The substrate treating liquid according to the present invention can be used for removing a liquid on a substrate such as a semiconductor substrate having a pattern-formed surface, and is characterized by including cyclohexanone oxime as a sublimable substance, and at least one solvent selected from the group consisting of alcohols, ketones, ethers, cycloalkanes and water.

7 Claims, No Drawings

SUBSTRATE TREATING METHOD

CROSS-REFERENCE TO RELATED APPLICATIONS

The present application is a Continuation of U.S. patent application Ser. No. 16/910,116, filed Jun. 24, 2020, by Yuta SASAKI, entitled SUBSTRATE TREATING LIQUID, which claims priority to Japanese Patent Application No. 2019-120655, filed on Jun. 28, 2019, the contents of which applications are incorporated by reference.

BACKGROUND OF THE INVENTION

Field of the Invention

The present invention relates to a substrate treating method, a substrate treating liquid and a substrate treating apparatus which remove, from substrates, liquids adhered to various types of substrates such as, for example, a semiconductor substrate, a substrate for a photomask glass, a substrate for a liquid crystal display glass, a substrate for a plasma display glass, a FED (Field Emission Display) substrate, a substrate for an optical disc, a substrate for a magnetic disc and a substrate for a magneto-optical disc.

Description of Related Art

In recent years, as a finer pattern has been formed on a substrate such as a semiconductor substrate, the aspect ratio of a projection in a pattern having recesses and projections (the ratio between the height and the width of the projection in the pattern) has been increased. Hence, there is a problem of a so-called pattern collapse in which, at the time of drying treatment, surface tension that acts on a boundary surface between a liquid such as a washing liquid or a rinse liquid in recesses in the pattern and a gas in contact with the liquid pulls and collapses the adjacent projections in the pattern.

Japanese Unexamined Patent Application Publication No. 2012-243869 discloses, as drying technology for the purpose of preventing such collapse of the pattern, for example, a substrate drying method in which a liquid on a substrate having a concave-convex pattern formed on the surface is removed and the substrate is dried. According to this substrate drying method, a solution of a sublimable substance is supplied onto a substrate and the inside of recesses of the pattern is filled with the solution, followed by drying of a solvent in the solution. Subsequently, the inside of recesses of the pattern is filled with the sublimable substance in a solid state and the temperature of the substrate is raised to the temperature higher than a sublimation temperature of the sublimable substance to remove the sublimable substance from the substrate. Japanese Unexamined Patent Application Publication No. 2012-243869 mentions that this makes it possible to inhibit stress, which attempts to collapse projections of the pattern formable due to surface tension of a liquid on the substrate, from acting on the projections of the pattern, thus leading to the prevention of pattern collapse.

Japanese Unexamined Patent Application Publication No. 2017-76817 discloses a method for producing a semiconductor device in which, in the case of sublimation drying of the surface of a semiconductor substrate having a fine pattern formed thereon, a solution prepared by dissolving a substance to be precipitated such as cyclohexane-1,2-dicarboxylic acid in a solvent such as an aliphatic hydrocarbon is used. This patent document mentions that this method for producing a semiconductor device enables the inhibition of pattern collapse during drying of a semiconductor substrate after a liquid treatment.

According to the sublimation drying methods disclosed in these patent documents, for example, it is possible to reduce the collapse rate of the pattern by rotating the substrate at a high speed, as compared with a method by spin drying in which a liquid adhered to the substrate surface is removed and a drying method in which a liquid adhered to the substrate surface is replaced by isopropyl alcohol (IPA) and IPA is removed by sublimation drying. However, when the pattern has extremely low mechanical strength, there may arise a problem of locally generating the region where pattern collapse occurs, even in the case of a conventional sublimation drying method.

BRIEF SUMMARY OF THE INVENTION

The present invention has been made in light of the foregoing problems, and an object thereof is to provide a substrate treating liquid capable of removing a liquid adhered to the surface of a substrate while preventing partial or local collapse of a pattern formed on the surface of the substrate.

In order to solve the above-mentioned problems, the substrate treating liquid according to the present invention is a substrate treating liquid which is used for removing a liquid on a substrate having a pattern-formed surface, comprises cyclohexanone oxime as a sublimable substance, and at least one solvent selected from the group consisting of alcohols, ketones, ethers, cycloalkanes and water.

When a liquid is present on a pattern-formed surface of a substrate, the substrate treating liquid with the configuration mentioned above enables the removal of the liquid while preventing a collapse of a pattern due to the principle of sublimation drying (or freeze-drying). In particular, the substrate treating liquid with the configuration mentioned above can satisfactorily inhibit the collapse of the pattern in the partial or local region of the pattern-formed surface of the substrate, as compared with a substrate treating liquid using a conventional sublimable substance, by including cyclohexanone oxime as the sublimable substance and a solvent such as alcohols. The substrate treating liquid with the configuration mentioned above can also inhibit the collapse of the pattern in the partial or local region, as compared with a conventional substrate treating liquid, even when the substrate has not only a hydrophobic pattern-formed surface but also a hydrophilic pattern-formed surface. The substrate treating liquid with the configuration mentioned above can also inhibit the collapse of the pattern in the partial or local region, as compared with a conventional substrate treating liquid, even when the substrate has a fine pattern with a large aspect ratio.

In this configuration, it is preferred that the content of the cyclohexanone oxime is in a range of 0.1% by volume or more and 10% by volume or less based on the total volume of the substrate treating liquid. By adjusting the content of cyclohexanone oxime to 0.1% by volume or more based on the total volume of the substrate treating liquid, it is possible to satisfactorily inhibit the collapse of the pattern in the partial or local region of the pattern-formed surface of the substrate. Meanwhile, by adjusting the content of cyclohexanone oxime to 10% by volume or less based on the total volume of the substrate treating liquid, it is possible to make the solubility of cyclohexanone oxime in the solvent at a normal temperature satisfactory, thus making it possible to uniformly dissolve the cyclohexanone oxime.

In this configuration, it is preferred that the solvent is at least one selected from the group consisting of methyl alcohol, ethyl alcohol, isopropyl alcohol, n-butyl alcohol, tert-butyl alcohol, cyclohexanol, acetone, propylene glycol monoethyl ether, propylene glycol monomethyl ether acetate, cyclohexane and water.

The substrate treating liquid of the present invention can inhibit the collapse of the pattern on the pattern-formed surface of the substrate, as compared with a substrate treating liquid containing a conventional sublimable substance, and particularly can satisfactorily inhibit the collapse of the pattern in the partial or local region of the pattern-formed surface. The substrate treating liquid can also satisfactorily inhibit the collapse of the pattern in the partial or local region, as compared with a conventional substrate treating liquid, even when the substrate has a hydrophilic pattern-formed surface, and the substrate has a fine pattern with a large aspect ratio.

DETAILED DESCRIPTION OF THE INVENTION (Substrate Treating Liquid)

The substrate treating liquid according to the embodiment of the present invention will be described below.

First, "substrate" as used herein refers to various substrates such as a semiconductor substrate, a substrate for a photomask glass, a substrate for a liquid crystal display glass, a substrate for a plasma display glass, a field emission display (FED) substrate, a substrate for an optical disc, a substrate for a magnetic disc, and a substrate for a magneto-optical disc. "Pattern-formed surface" as used herein means a surface in which a concave-convex pattern is formed in an arbitrary region in the substrate regardless of the surface with a planar shape, a curved shape or a concave-convex shape. "Sublimable" as used herein means that a single substance, a compound or a mixture has the property of changing its phase from a solid phase to a gas phase or from a gas phase to a solid phase without the intervention of a liquid phase, and "sublimable substance" means a substance which has the sublimation property mentioned above.

The substrate treating liquid according to the present embodiment includes at least cyclohexanone oxime and a solvent. In a drying treatment for removing a liquid which is present in the pattern-formed surface of the substrate, the substrate treating liquid according to the present embodiment performs a function which assists the drying treatment.

Cyclohexanone oxime is represented by the following chemical formula (1) and can function as the sublimable substance in the substrate treating liquid according to the present embodiment.

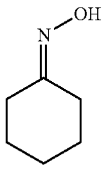

(1)

Cyclohexanone oxime has the following physical property values: a freezing point of 90.5° C., a boiling point of 210° C., a vapor pressure of 0.00717 Torr to 251.458 Torr (0.96 Pa to 33.52 kPa), a melting entropy ΔS of 30.0 J/mol·K, and an n-octanol/water partition coefficient of +1.2. When the freezing point is a freezing point possessed by cyclohexanone oxime, it is possible to prevent poor solidification (freezing) due to freezing point depression at a narrow place of the pattern-formed surface. It is also possible to eliminate the need for a coolant in the case of solidification.

It is preferable that cyclohexanone oxime is present in the substrate treating liquid in a state of being dissolved in a solvent.

The content of cyclohexanone oxime is appropriately set, for example, according to supplying conditions when the substrate treating liquid is supplied onto a pattern-formed surface of the substrate, and is preferably 0.1% by volume or more and 10% by volume or less, more preferably 1.25% by volume or more and 5% by volume or less, and particularly preferably 2% by volume or more and 4% by volume or less, based on the total volume of the substrate treating liquid. By setting the content of cyclohexanone oxime at 0.1% by volume or more, it is possible to more satisfactorily inhibit the collapse of the pattern in the partial or local region even to the substrate having a fine pattern with a large aspect ratio. Meanwhile, by setting the content of cyclohexanone oxime at 10% by volume or less, it becomes possible to make the solubility of cyclohexanone oxime in the solvent at a normal temperature satisfactory, thus making it possible to uniformly dissolve the cyclohexanone oxime. "Normal temperature" as used herein means a temperature in a range of 5° C. to 35° C. "Solubility" as used herein means that 10 g or more of cyclohexanone oxime is dissolved in 100 g of the solvent at 23° C.

The solvent can function as a solvent which dissolves cyclohexanone oxime. Specifically, the solvent is at least one selected from the group consisting of alcohols, ketones, ethers, cycloalkanes and water.

Examples of alcohols mentioned above include, but are not particularly limited to, methyl alcohol (melting point: −98° C., n-octanol/water partition coefficient: −0.82 to −0.66), ethyl alcohol (melting point: −117° C., n-octanol/water partition coefficient: −0.32), isopropyl alcohol (melting point: −90° C., n-octanol/water partition coefficient: +0.05), n-butyl alcohol (melting point: −90° C., n-octanol/water partition coefficient: +0.88), tert-butyl alcohol (melting point: 25° C., n-octanol/water partition coefficient: +0.3), cyclohexanol (melting point: 23° C. to 25° C., n-octanol/water partition coefficient: +1.2) and the like.

Examples of ketones mentioned above include, but are not particularly limited to, acetone (melting point: −95° C., n-octanol/water partition coefficient: −0.24) and the like.

Examples of ethers mentioned above include, but are not particularly limited to, propylene glycol monoethyl ether (melting point: −100° C., n-octanol/water partition coefficient: +0.3), propylene glycol monomethyl ether acetate (melting point: −87° C., n-octanol/water partition coefficient: +0.43) and the like.

Examples of cycloalkanes mentioned above include, but are not particularly limited to, cyclohexane (melting point: 7° C., n-octanol/water partition coefficient: +3.4) and the like.

Examples of water mentioned above include, but are not particularly limited to, pure water and the like.

All solvents exemplified above can be used alone or in combination with cyclohexanone oxime. It is also possible to use two or more solvents exemplified above in combination with cyclohexanone oxime.

The solvent is preferably a solvent such that cyclohexanone oxime exhibits satisfactory solubility.

Of the solvents exemplified above, isopropyl alcohol or the like is preferably exemplified from the viewpoint of being capable of satisfactorily inhibiting pattern collapse in the partial or local region.

The n-octanol/water partition coefficient of the solvent is preferably in a range of −0.85 to +3.4, more preferably −0.82 to +2.2, still more preferably −0.82 to +1.2, and particularly preferably 0 to +1.2.

The vapor pressure at a normal temperature of the solvent is preferably 500 Pa or more, more preferably 1,000 Pa or more, and particularly preferably 5,000 Pa or more. The more a difference between the vapor pressure and the above vapor pressure of cyclohexanone oxime increases, it becomes possible to form a solidified film even when cyclohexanone oxime has low concentration, thus enabling reduction in processing costs and reduction in residue. From the viewpoint of reducing load on piping due to the vapor pressure, the vapor pressure of the solvent is preferably set at 10 kPa or less.

(Method for Producing Substrate Treating Liquid and Storage Method)

Examples of the method for producing a substrate treating liquid according to the present embodiment include, but are not particularly limited to, a method in which crystals of cyclohexanone oxime are added to a solvent at a normal temperature under atmospheric pressure such that a fixed content is achieved. The environment "under atmospheric pressure" means an environment under a pressure of 0.7 atm or more and 1.3 atm or less with the standard atmospheric pressure (1 atmosphere, 1,013 hPa) in the center.

In the method for producing a substrate treating liquid, filtration may be performed after adding crystals of cyclohexanone oxime to the solvent. This makes it possible to reduce or prevent the generation of the residue derived from the substrate treating liquid on the pattern-formed surface when the substrate treating liquid is supplied onto the pattern-formed surface of the substrate and used for removing the liquid. There is no particular limitation on the filtration method and, for example, filtration with a filter can be employed.

The substrate treating liquid according to the present embodiment can be stored at a normal temperature. From the viewpoint of inhibiting a change in concentration of cyclohexanone oxime due to evaporation of the solvent, it is preferable to store the substrate treating liquid at low temperature, e.g., about 5° C. When using the substrate treating liquid stored at low temperature, the substrate treating liquid is preferably used after controlling the liquid temperature of the substrate treating liquid to the operating temperature or room temperature, from the viewpoint of preventing mixing of moisture due to condensation.

(Method for Using Substrate Treating Liquid)

The substrate treating liquid according to the present embodiment can be used, for example, for removing a liquid on a substrate having a pattern-formed surface.

Examples of the liquid to be removed include isopropyl alcohol (IPA) or the like which is replaced from a washing liquid so as to remove the washing liquid for washing the pattern-formed surface of the substrate.

More specifically, first, the substrate treating liquid according to the present embodiment is applied onto a pattern-formed surface of the substrate to which IPA is adhered, thus forming a liquid film of the substrate treating liquid. The substrate treating liquid is preferably supplied while rotating the substrate around, as a rotation axis, a vertical direction in the center of the substrate. In this case, the substrate treating liquid can be supplied from above the center of the substrate. The substrate treating liquid thus supplied onto the surface of the substrate flows toward the periphery of the substrate from the vicinity of the center of the surface of the substrate by a centrifugal force generated by the rotation of the substrate, thus enabling diffusion over the surface of the substrate. The rotation speed of the substrate can vary depending on the amount of the substrate treating liquid supplied, the content of cyclohexanone oxime in the substrate treating liquid, the thickness of the liquid film of the substrate treating liquid and the like. Usually, the rotation speed of the substrate is appropriately selected in a range of 100 rpm to 3,000 rpm.

Subsequently, the liquid film of the substrate treating liquid is solidified to form a solidified film of the substrate treating liquid, more specifically, cyclohexanone oxime. Examples of the solidification method include, but are not particularly limited to, a method in which the solvent in the substrate treating liquid is evaporated by continuously rotating the substrate, thus precipitating cyclohexanone oxime. In the case of this method, usually, the rotation speed of the substrate is appropriately selected in a range of 100 rpm to 3,000 rpm.

Other solidification methods also include a method in which a nitrogen gas is blown from above the substrate treating liquid and a solvent, which is present as a gas above the substrate, is exhausted and thus the solvent in the substrate treating liquid is evaporated (volatilized). In this case, the temperature of the nitrogen gas can be set in a range of 0° C. to 80° C. The nitrogen gas is preferably suppled while rotating the substrate, similar to the case where the substrate treating liquid is supplied. The rotation speed of the substrate can vary depending on the amount of the nitrogen gas supplied. Usually, the rotation speed of the substrate is appropriately selected in a range of 100 rpm to 3,000 rpm. The liquid film of the substrate treating liquid may be solidified under cooling by being directly brought into contact with the nitrogen gas.

It is also possible to employ, as the solidification method of the liquid film of the substrate treating liquid, in addition to a solvent evaporation method using the nitrogen gas, a method in which the liquid film of the substrate treating liquid is cooled by bringing cold water into contact with the back side of the substrate, a method in which the solvent in the substrate treating liquid is evaporated by bringing warm water into contact with the back side of the substrate, thus leading to the precipitation of cyclohexanone oxime, and the like. In the case of the cooling method using cold water, the temperature of cold water can be set, for example, in a range of 0° C. to 20° C. In the case of the precipitation method of cyclohexanone oxime using warm water, the temperature of warm water can be set, for example, in a range of 25° C. to 80° C.

Subsequently, the solidified film is sublimed in a gas state without passing through a liquid state to remove the solidified film. Examples of the sublimation method include, but are not particularly limited to, a method in which a nitrogen gas is contacted by directly blowing over the liquid film of the substrate treating liquid, and the like. In this case, the temperature of the nitrogen gas can be set, for example, in a range of 0° C. to 80° C. The nitrogen gas is preferably supplied while rotating the substrate, similar to the case where the liquid film of the substrate treating liquid is solidified. The rotation speed of the substrate can vary depending on the amount of the nitrogen gas supplied and the like. Usually, the rotation speed of the substrate is appropriately selected in a range of 100 rpm to 3,000 rpm. The solidified film is naturally sublimated without blowing over the nitrogen gas, and the nitrogen gas is preferably brown from the viewpoint of shortening the drying time (the time until the solidified film is removed by sublimation after the formation of the solidified film) leading to an improvement in throughput.

As mentioned above, by performing a sublimation drying treatment using the substrate treating liquid according to the present embodiment, it is possible to remove a liquid such as IPA while inhibiting the collapse of a concave-convex pattern in the pattern-formed surface of the substrate. In particular, the substrate treating liquid according to the present embodiment can satisfactorily inhibit the collapse of the pattern in the partial or local region of the pattern-formed surface of the substrate, as compared with a substrate treating liquid containing a conventional sublimable substance, even when the substrate has a hydrophilic pattern-formed surface, and the substrate has a fine pattern with a large aspect ratio.

(Other Matters)

In the present embodiment, a description has been given of the aspect in which cyclohexanone oxime is present in a state of being dissolved in the substrate treating liquid. However, the present invention is not limited to this aspect and, for example, cyclohexanone oxime may be present in the substrate treating liquid in a molten state. "Molten state" as used herein means a state where cyclohexanone oxime is completely or partially melted to have fluidity and thus cyclohexanone oxime is in a liquid state.

When cyclohexanone oxime is included in the substrate treating liquid in a molten state, of the solvents exemplified above, preferred is a solvent with which cyclohexanone oxime in the molten state exhibits.

Preferred examples of the present invention will be illustratively described in detail below. However, unless otherwise restrictively described, materials, amounts and the like mentioned in the respective Examples are not intended to limit the scope of the present invention.

(Substrate)

As a substrate, silicon substrates A and B having a model pattern formed on the surface was prepared, both substrates having a diameter of 300 mm. On the silicon substrate A, a pattern is formed in a manner such that cylinders each having an aspect ratio of 18.4 are arranged at intervals of about 17.7 nm. On the silicon substrate B, a pattern is formed in a manner such that cylinders each having an aspect ratio of 22.6 are arranged at intervals of about 16.7 nm.

Example 1

In the present example, the silicon substrate B was subjected to a drying treatment by the following procedure, and the effect of inhibiting pattern collapse was evaluated.

<Washing Step/IPA Rinsing Step>

First, an aqueous hydrofluoric acid solution (volume ratio; hydrogen fluoride:water=1:10) as a washing liquid was supplied onto a pattern-formed surface (surface) of the silicon substrate B and then the pattern-formed surface was washed. Subsequently, deionized water (DIW) was supplied onto the washed pattern-formed surface of the silicon substrate B, and the pattern-formed surface was rinsed by replacing the washing liquid by DIW.

Moreover, IPA was supplied onto the pattern-formed surface of the silicon substrate B. IPA was supplied while rotating the silicon substrate B around, as a rotation axis, a vertical direction in the center of the silicon substrate B. IPA was supplied from the vertical direction in the center of the silicon substrate B. Whereby, DIW on the pattern-formed surface of the silicon substrate B was replaced by IPA. The rotation speed of the silicon substrate B was set at 500 rpm.

<Supplying Step of Substrate Treating Liquid>

Subsequently, a substrate treating liquid having a liquid temperature of 23° C. was supplied onto the pattern-formed surface of the silicon substrate B, to which IPA is adhered. The substrate treating liquid was supplied while rotating the silicon substrate B around, as a rotation axis, a vertical direction in the center of the silicon substrate B. The substrate treating liquid was supplied from the vertical direction in the center of the silicon substrate B. The substrate treating liquid thus supplied onto the surface of the silicon substrate B flows toward the periphery of the silicon substrate B from the vicinity of the center of the surface of the silicon substrate B by a centrifugal force generated by the rotation of the silicon substrate B, thus enabling diffusion over the surface of the silicon substrate B. As a result, IPA adhered on the pattern-formed surface was replaced by the substrate treating liquid to form a liquid film made of the substrate treating liquid. The rotation speed of the silicon substrate B was set at 300 rpm. The time from the starting of supplying of the substrate treating liquid to the formation of the liquid film of the substrate treating liquid was set at 30 seconds.

As the substrate treating liquid, a liquid prepared by dissolving cyclohexanone oxime in isopropyl alcohol as a solvent was used. The content of cyclohexanone oxime was set at 0.76% by volume based on the total volume of the substrate treating liquid.

<Solidified Film Forming Step>

Subsequently, a nitrogen gas at 7° C. was supplied onto the surface of the silicon substrate B on which the liquid film of the substrate treating liquid is formed. The nitrogen gas was supplied while rotating the silicon substrate B around, as a rotation axis, a vertical direction in the center of the silicon substrate B. The nitrogen gas was supplied from the vertical direction in the center of the silicon substrate B. Whereby, the nitrogen gas supplied onto the surface of the silicon substrate B is diffused toward the periphery of the silicon substrate B from the vicinity of the center of the surface of the silicon substrate B by a centrifugal force generated by the rotation of the silicon substrate B, thus performing solvent evaporation to the liquid film made of the substrate treating liquid formed on the pattern-formed surface. The liquid film was solidified (precipitated) by this solvent evaporation of the liquid film to form an amorphous solidified film having high visible light transmittance. The rotation speed of the silicon substrate B was set at 300 rpm. The silicon substrate B was rotated until the solidified film is formed. The amount of the nitrogen gas supplied was set at 40 L/min.

<Sublimation Step>

Subsequently, even after the solidification of the substrate treating liquid, the nitrogen gas at 7° C. was continuously supplied while rotating the silicon substrate B, and the solidified film was sublimated. The rotation speed of the silicon substrate B was set at 1,500 rpm. The amount of the nitrogen gas supplied was set at 40 L/min, and the supplying time of nitrogen gas was set at 300 seconds. As mentioned above, the solidified film was removed from the pattern-formed surface of the silicon substrate B, followed by sublimation drying.

<Evaluation of Effect of Inhibiting Pattern Collapse>

After confirming the removal of the solidified film, a collapse rate of the pattern on the silicon substrate B was calculated, and the effect of inhibiting pattern collapse on the pattern-formed surface was evaluated by the collapse rate. Specifically, the total number of projections and the number of projections collapsed in the SEM image were counted by a scanning electron microscope (manufactured by Hitachi High-Technologies, Japan, Model number: S-4800) and then the collapse rate of the pattern was calculated by the following formula. As a result, the collapse rate of the pattern was 3.2%. The occurrence of collapse (unevenness in collapse) of the pattern in the partial or local region was not confirmed on the pattern-formed surface. The results are shown in Table 1.

Collapse rate (%)=(number of projections collapsed in arbitrary region)/(total number of projections in the region)×100

The criterion for evaluating the treating in Table 1 is as follows.

Very good: The pattern collapse rate is in the range of 0% or more and 1% or less.

Good: The pattern collapse rate is in the range of greater than 1% and 5% or less.

Failure: The pattern collapse rate is in a range greater than 5%.

Reference Example 1

In the present reference example, a silicon substrate A was used as the substrate. The content of cyclohexanone oxime was changed to 1.25% by volume based on the total volume of the substrate treating liquid. Moreover, the rotation speed of the silicon substrate A when the substrate treating liquid is supplied onto the pattern-formed surface of the silicon substrate A was changed to 0 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 100.00%.

Example 2

In the present example, a silicon substrate A was used as the substrate. The content of cyclohexanone oxime was changed to 1.25% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0.42%. The occurrence of collapse (unevenness in collapse) of the pattern in the partial or local region was not confirmed on the pattern-formed surface.

Example 3

In the present example, a silicon substrate A was used as the substrate. The content of cyclohexanone oxime was changed to 1.25% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 1.28%. The occurrence of collapse (unevenness in collapse) of the pattern in the partial or local region was not confirmed on the pattern-formed surface.

Example 4

In the present example, the content of cyclohexanone oxime was changed to 1.25% by volume based on the total volume of the substrate treating liquid. Moreover, the rotation speed of the silicon substrate B when the substrate treating liquid is supplied onto the pattern-formed surface of the silicon substrate B was changed to 1,000 rpm. In the same manner as in Example 1 except for that, a drying treatment of the silicon substrate B was performed. By the same method as in Example 1, the effect of inhibiting pattern collapse was also evaluated. As a result, the collapse rate of the pattern was 0.89%. The occurrence of collapse (unevenness in collapse) of the pattern in the partial or local region was not confirmed on the pattern-formed surface.

Example 5

In the present example, a silicon substrate A was used as the substrate. The content of cyclohexanone oxime was changed to 1.25% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 1.47%. The occurrence of collapse (unevenness in collapse) of the pattern in the partial or local region was not confirmed on the pattern-formed surface.

Example 6

In the present example, a silicon substrate A was used as the substrate. The content of cyclohexanone oxime was changed to 1.25% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 1.7%. The occurrence of collapse (unevenness in collapse) of the pattern in the partial or local region was not confirmed on the pattern-formed surface.

Reference Example 2

In the present reference example, a silicon substrate A was used as the substrate. The content of cyclohexanone oxime was changed to 1.25% by volume based on the total volume of the substrate treating liquid. Moreover, the rotation speed of the silicon substrate A when the substrate treating liquid is supplied onto the pattern-formed surface of the silicon substrate A was changed to 2,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 100.00%.

Reference Example 3

In the present reference example, a silicon substrate A was used as the substrate. The content of cyclohexanone oxime was changed to 1.25% by volume based on the total volume of the substrate treating liquid. Moreover, the rotation speed of the silicon substrate A when the substrate treating liquid is supplied onto the pattern-formed surface of the silicon substrate A was changed to 3,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 100.00%.

Reference Example 4

In the present reference example, a silicon substrate A was used as the substrate. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 0 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 100.00%.

Reference Example 5

In the present reference example, a silicon substrate A was used as the substrate. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 100.00%.

Example 7

In the present example, a silicon substrate A was used as the substrate. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0.56%. The occurrence of collapse (unevenness in collapse) of the pattern in the partial or local region was not confirmed on the pattern-formed surface.

Example 8

In the present example, a silicon substrate A was used as the substrate. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0.72%. The occurrence of collapse (unevenness in collapse) of the pattern in the partial or local region was not confirmed on the pattern-formed surface.

Example 9

In the present example, a silicon substrate A was used as the substrate. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0.52%. The occurrence of collapse (unevenness in collapse) of the pattern in the partial or local region was not confirmed on the pattern-formed surface.

Example 10

In the present example, a silicon substrate A was used as the substrate. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 2,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 3.86%. The occurrence of collapse (unevenness in collapse) of the pattern in the partial or local region was not confirmed on the pattern-formed surface.

Example 11

In the present example, a silicon substrate A was used as the substrate. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 3,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 2.16%. The occurrence of collapse (unevenness in collapse) of the pattern in the partial or local region was not confirmed on the pattern-formed surface.

Reference Example 6

In the present reference example, a silicon substrate A was used as the substrate. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 0 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 100.00%.

Reference Example 7

In the present reference example, a silicon substrate A was used as the substrate. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 99.80%. The occurrence of collapse (unevenness in collapse) of the pattern in the partial or local region was confirmed on the pattern-formed surface.

Reference Example 8

In the present reference example, a silicon substrate A was used as the substrate. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 13.10%. The occurrence of collapse (unevenness in collapse) of the pattern in the partial or local region was confirmed on the pattern-formed surface.

Example 12

In the present example, a silicon substrate A was used as the substrate. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0.44%. The occurrence of collapse (unevenness in collapse) of the pattern in the partial or local region was not confirmed on the pattern-formed surface.

Example 13

In the present example, a silicon substrate A was used as the substrate. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 3,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0.56%. The occurrence of collapse (unevenness in collapse) of the pattern in the partial or local region was not confirmed on the pattern-formed surface.

(Results 1)

As shown in Tables 1 to 3, in the substrate treating liquids of Examples 1 to 13 in which cyclohexanone oxime was used as the sublimable substance and N-butyl alcohol was used as the solvent, by performing a substrate treatment under appropriate conditions for the content of sublimable substance, the amount of substrate treating liquid supplied and the rotation speed of the silicon substrate in the supplying step of the substrate treating liquid, it has been confirmed that it is possible to inhibit the pattern from partially or locally collapsing on the pattern-formed surface, and to reduce the pattern collapse rate.

TABLE 1

| | Example 1 | Reference Example 1 | Example 2 | Example 3 | Example 4 | Example 5 | Example 6 | Reference Example 2 | Reference Example 3 |
|---|---|---|---|---|---|---|---|---|---|
| Sublimable substance | Cyclohexanone oxime | | | | | | | | |
| Solvent | Isopropyl alcohol | | | | | | | | |
| Content of sublimable substance (% by volume) | 0.76 | 1.25 | 1.25 | 1.25 | 1.25 | 1.25 | 1.25 | 1.25 | 1.25 |
| Type of silicon substrate | B | A | A | A | B | A | A | A | A |
| Rotation speed in supplying step (rpm) | 300 | 0 | 500 | 1,000 | 1,000 | 1,500 | 2,000 | 2,500 | 3,000 |
| Pattern collapse rate (%) | 3.2 | 100.00 | 0.42 | 1.28 | 0.89 | 1.47 | 1.7 | 100.00 | 100.00 |
| Presence or absence of unevenness in collapse of pattern | Absent | Absent | Absent | Absent | Absent | Absent | Absent | Absent | Absent |
| Evaluation of treating | Good | Failure | Very good | Good | Very good | Good | Good | Failure | Failure |

TABLE 2

| | Reference Example 4 | Reference Example 5 | Example 7 | Example 8 | Example 9 | Example 10 | Example 11 |
|---|---|---|---|---|---|---|---|
| Sublimable substance | Cyclohexanone oxime | | | | | | |
| Solvent | Isopropyl alcohol | | | | | | |
| Content of sublimable substance (% by volume) | 2.5 | 2.5 | 2.5 | 2.5 | 2.5 | 2.5 | 2.5 |
| Type of silicon substrate | A | A | A | A | A | A | A |
| Rotation speed in supplying step (rpm) | 0 | 500 | 1,000 | 1,500 | 2,000 | 2,500 | 3,000 |
| Pattern collapse rate (%) | 100.00 | 100.00 | 0.56 | 0.72 | 0.52 | 3.86 | 2.16 |
| Presence or absence of unevenness in collapse of pattern | Absent | Absent | Absent | Absent | Absent | Absent | Absent |
| Evaluation of treating | Failure | Failure | Very good | Very good | Very good | Good | Good |

TABLE 3

| | Reference Example 6 | Reference Example 7 | Reference Example 8 | Example 12 | Example 13 |
|---|---|---|---|---|---|
| Sublimable substance | Cyclohexanone oxime | | | | |
| Solvent | Isopropyl alcohol | | | | |
| Content of sublimable substance (% by volume) | 5 | 5 | 5 | 5 | 5 |
| Type of silicon substrate | A | A | A | A | A |
| Rotation speed in supplying step (rpm) | 0 | 5,00 | 1,000 | 2,000 | 3,000 |
| Pattern collapse rate (%) | 100.00 | 99.80 | 13.10 | 0.44 | 0.56 |
| Presence or absence of unevenness in collapse of pattern | Absent | Present | Present | Absent | Absent |
| Evaluation of treating | Failure | Failure | Failure | Very good | Very good |

Reference Example 9

In the present reference example, a silicon substrate A was used as the substrate. N-butyl alcohol was used as the solvent of the substrate treating liquid. The content of cyclohexanone oxime was changed to 10% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 12.22%. The occurrence of collapse (unevenness in collapse) of the pattern in the partial or local region was confirmed on the pattern-formed surface.

Reference Example 10

In the present reference example, a silicon substrate A was used as the substrate. N-butyl alcohol was used as the solvent of the substrate treating liquid. The content of cyclohexanone oxime was changed to 10% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 22.91%. The occurrence of collapse (unevenness in collapse) of the pattern in the partial or local region was confirmed on the pattern-formed surface.

Reference Example 11

In the present reference example, a silicon substrate A was used as the substrate. N-butyl alcohol was used as the solvent of the substrate treating liquid. The content of cyclohexanone oxime was changed to 10% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 12.19%. The occurrence of collapse (unevenness in collapse) of the pattern in the partial or local region was confirmed on the pattern-formed surface.

Example 14

In the present example, a silicon substrate A was used as the substrate. N-butyl alcohol was used as the solvent of the substrate treating liquid. The content of cyclohexanone oxime was changed to 10% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0%. The occurrence of collapse (unevenness in collapse) of the pattern in the partial or local region was not confirmed on the pattern-formed surface.

Reference Example 12

In the present reference example, a silicon substrate A was used as the substrate. N-butyl alcohol was used as the solvent of the substrate treating liquid. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 98.80%. The occurrence of collapse (unevenness in collapse) of the pattern in the partial or local region was confirmed on the pattern-formed surface.

Example 15

In the present example, a silicon substrate A was used as the substrate. N-butyl alcohol was used as the solvent of the substrate treating liquid. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 3.92%. The occurrence of collapse (unevenness in collapse) of the pattern in the partial or local region was not confirmed on the pattern-formed surface.

Example 16

In the present example, a silicon substrate A was used as the substrate. N-butyl alcohol was used as the solvent of the substrate treating liquid. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0%. The occurrence of collapse (unevenness in collapse) of the pattern in the partial or local region was not confirmed on the pattern-formed surface.

Example 17

In the present example, a silicon substrate A was used as the substrate. N-butyl alcohol was used as the solvent of the substrate treating liquid. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0%. The occurrence of collapse (unevenness in collapse) of the pattern in the partial or local region was not confirmed on the pattern-formed surface.

Reference Example 13

In the present reference example, a silicon substrate A was used as the substrate. N-butyl alcohol was used as the solvent of the substrate treating liquid. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 99.14%. The occurrence of collapse (unevenness in collapse) of the pattern in the partial or local region was confirmed on the pattern-formed surface.

Reference Example 14

In the present reference example, a silicon substrate A was used as the substrate. N-butyl alcohol was used as the solvent of the substrate treating liquid. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 13.41%. The occurrence of collapse (unevenness in collapse) of the pattern in the partial or local region was not confirmed on the pattern-formed surface.

Reference Example 15

In the present reference example, a silicon substrate A was used as the substrate. N-butyl alcohol was used as the solvent of the substrate treating liquid. The content of cyclohexanone oxime was changed to 2.5% by volume based on the total volume of the substrate treating liquid.

Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 87.19%. The occurrence of collapse (unevenness in collapse) of the pattern in the partial or local region was not confirmed on the pattern-formed surface.

Reference Example 16

In the present reference example, a silicon substrate A was used as the substrate. N-butyl alcohol was used as the solvent of the substrate treating liquid. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 66.60%. The occurrence of collapse (unevenness in collapse) of the pattern in the partial or local region was not confirmed on the pattern-formed surface.

(Results 2)

As shown in Tables 4 to 6, in the substrate treating liquids of Examples 14 to 17 in which cyclohexanone oxime was used as the sublimable substance and N-butyl alcohol was used as the solvent, by performing a substrate treatment under appropriate conditions for the content of sublimable substance, the amount of substrate treating liquid supplied and the rotation speed of the silicon substrate in the supplying step of the substrate treating liquid, it has been confirmed that it is possible to inhibit the pattern from partially or locally collapsing on the pattern-formed surface, and to reduce the pattern collapse rate.

TABLE 4

| | Reference Example 9 | Reference Example 10 | Reference Example 11 | Example 14 |
|---|---|---|---|---|
| Sublimable substance | Cyclohexanone oxime | | | |
| Solvent | N-butyl alcohol | | | |
| Content of sublimable substance (% by volume) | 10 | 10 | 10 | 10 |
| Type of silicon substrate | A | A | A | A |
| Rotation speed in supplying step (rpm) | 500 | 1,000 | 1,500 | 2,000 |
| Pattern collapse rate (%) | 12.22 | 22.91 | 12.19 | 0.00 |
| Presence or absence of unevenness in collapse of pattern | Present | Present | Present | Absent |
| Evaluation of treating | Failure | Failure | Failure | Very good |

TABLE 5

| | Reference Example 12 | Example 15 | Example 16 | Example 17 |
|---|---|---|---|---|
| Sublimable substance | Cyclohexanone oxime | | | |
| Solvent | N-butyl alcohol | | | |
| Content of sublimable substance (% by volume) | 5 | 5 | 5 | 5 |
| Type of silicon substrate | A | A | A | A |
| Rotation speed in supplying step (rpm) | 500 | 1,000 | 1,500 | 2,000 |
| Pattern collapse rate (%) | 98.80 | 3.92 | 0.00 | 0.00 |
| Presence or absence of unevenness in collapse of pattern | Present | Absent | Absent | Absent |
| Evaluation of treating | Failure | Good | Very good | Very good |

TABLE 6

| | Reference Example 13 | Reference Example 14 | Reference Example 15 | Reference Example 16 |
|---|---|---|---|---|
| Sublimable substance | Cyclohexanone oxime | | | |
| Solvent | N-butyl alcohol | | | |
| Content of sublimable substance (% by volume) | 2.5 | 2.5 | 2.5 | 2.5 |
| Type of silicon substrate | A | A | A | A |
| Rotation speed in supplying step (rpm) | 500 | 1,000 | 1,500 | 2,000 |
| Pattern collapse rate (%) | 99.14 | 13.41 | 87.19 | 66.60 |
| Presence or absence of unevenness in collapse of pattern | Present | Absent | Absent | Absent |
| Evaluation of treating | Failure | Failure | Failure | Failure |

Example 18

In the present example, a silicon substrate A was used as the substrate. Propylene glycol monomethyl ether acetate (PGMEA) was used as the solvent of the substrate treating liquid. The content of cyclohexanone oxime was changed to 10% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 4.32%. The occurrence of collapse (unevenness in collapse) of the pattern in the partial or local region was not confirmed on the pattern-formed surface.

Reference Example 17

In the present reference example, a silicon substrate A was used as the substrate. PGMEA was used as the solvent of the substrate treating liquid. The content of cyclohexanone oxime was changed to 10% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 91.90%. The occurrence of collapse (unevenness in collapse) of the pattern in the partial or local region was confirmed on the pattern-formed surface.

Reference Example 18

In the present reference example, a silicon substrate A was used as the substrate. PGMEA was used as the solvent of the substrate treating liquid. The content of cyclohexanone oxime was changed to 10% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 13.36%. The occurrence of collapse (unevenness in collapse) of the pattern in the partial or local region was confirmed on the pattern-formed surface.

Reference Example 19

In the present reference example, a silicon substrate A was used as the substrate. PGMEA was used as the solvent of the substrate treating liquid. The content of cyclohexanone oxime was changed to 10% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 76.49%. The occurrence of collapse (unevenness in collapse) of the pattern in the partial or local region was confirmed on the pattern-formed surface.

Reference Example 20

In the present reference example, a silicon substrate A was used as the substrate. PGMEA was used as the solvent of the substrate treating liquid. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 83.27%. The occurrence of collapse (unevenness in collapse) of the pattern in the partial or local region was confirmed on the pattern-formed surface.

Example 19

In the present example, a silicon substrate A was used as the substrate. PGMEA was used as the solvent of the substrate treating liquid. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 4.85%. The occurrence of collapse (unevenness in collapse) of the pattern in the partial or local region was not confirmed on the pattern-formed surface.

Example 20

In the present example, a silicon substrate A was used as the substrate. PGMEA was used as the solvent of the substrate treating liquid. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 0%. The occurrence of collapse (unevenness in collapse) of the pattern in the partial or local region was not confirmed on the pattern-formed surface.

Example 21

In the present example, a silicon substrate A was used as the substrate. PGMEA was used as the solvent of the substrate treating liquid. The content of cyclohexanone oxime was changed to 5% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 4.98%. The occurrence of collapse (unevenness in collapse) of the pattern in the partial or local region was not confirmed on the pattern-formed surface.

Reference Example 21

In the present reference example, a silicon substrate A was used as the substrate. PGMEA was used as the solvent of the substrate treating liquid. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 25.43%. The occurrence of collapse (unevenness in collapse) of the pattern in the partial or local region was not confirmed on the pattern-formed surface.

Reference Example 22

In the present reference example, a silicon substrate A was used as the substrate. PGMEA was used as the solvent of the substrate treating liquid. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 1,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 99.14%. The occurrence of collapse (unevenness in collapse) of the pattern in the partial or local region was not confirmed on the pattern-formed surface.

Reference Example 23

In the present reference example, a silicon substrate A was used as the substrate. PGMEA was used as the solvent of the substrate treating liquid. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 100%.

Reference Example 24

In the present reference example, a silicon substrate A was used as the substrate. PGMEA was used as the solvent of the substrate treating liquid. The content of cyclohexanone oxime was changed to 2.5% by volume based on the total volume of the substrate treating liquid. Moreover, the rotation speed of the silicon substrate A when the substrate treating liquid is supplied onto the pattern-formed surface of the silicon substrate A was changed to 2,000 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 99.07%. The occurrence of collapse (unevenness in collapse) of the pattern in the partial or local region was not confirmed on the pattern-formed surface.

(Results 3)

As shown in Tables 7 to 9, in the substrate treating liquids of Examples 18 to 21 in which cyclohexanone oxime was used as the sublimable substance and N-butyl alcohol was used as the solvent, by performing a substrate treatment under appropriate conditions for the content of sublimable substance, the amount of substrate treating liquid supplied and the rotation speed of the silicon substrate in the supplying step of the substrate treating liquid, it has been confirmed that it is possible to inhibit the pattern from partially or locally collapsing on the pattern-formed surface, and to reduce the pattern collapse rate.

TABLE 7

| | Example 18 | Reference Example 17 | Reference Example 18 | Reference Example 19 |
|---|---|---|---|---|
| Sublimable substance | Cyclohexanone oxime | | | |
| Solvent | Propylene glycol monomethyl ether acetate | | | |
| Content of sublimable substance (% by volume) | 10 | 10 | 10 | 10 |
| Type of silicon substrate | A | A | A | A |
| Rotation speed in supplying step (rpm) | 500 | 1,000 | 1,500 | 2,000 |
| Pattern collapse rate (%) | 4.32 | 91.90 | 13.36 | 76.49 |
| Presence or absence of unevenness in collapse of pattern | Absent | Present | Present | Present |
| Evaluation of treating | Good | Failure | Failure | Failure |

TABLE 8

| | Reference Example 20 | Example 19 | Example 20 | Example 21 |
|---|---|---|---|---|
| Sublimable substance | Cyclohexanone oxime | | | |
| Solvent | Propylene glycol monomethyl ether acetate | | | |
| Content of sublimable substance (% by volume) | 5 | 5 | 5 | 5 |
| Type of silicon substrate | A | A | A | A |
| Rotation speed in supplying step (rpm) | 500 | 1,000 | 1,500 | 2,000 |
| Pattern collapse rate (%) | 83.27 | 4.85 | 0.00 | 4.98 |
| Presence or absence of unevenness in collapse of pattern | Present | Absent | Absent | Absent |
| Evaluation of treating | Failure | Good | Very good | Good |

TABLE 9

| | Reference Example 21 | Reference Example 22 | Reference Example 23 | Reference Example 24 |
|---|---|---|---|---|
| Sublimable substance | Cyclohexanone oxime | | | |
| Solvent | Propylene glycol monomethyl ether acetate | | | |
| Content of sublimable substance (% by volume) | 2.5 | 2.5 | 2.5 | 2.5 |
| Type of silicon substrate | A | A | A | A |
| Rotation speed in supplying step (rpm) | 500 | 1,000 | 1,500 | 2,000 |
| Pattern collapse rate (%) | 25.43 | 99.14 | 1000.0 | 99.07 |
| Presence or absence of unevenness in collapse of pattern | Absent | Absent | Absent | Absent |
| Evaluation of treating | Failure | Failure | Failure | Failure |

Comparative Example 1

In the present comparative example, a silicon substrate A was used as the substrate. A substrate treating liquid used as the substrate treating liquid was prepared by dissolving camphor (melting point: 175° C. to 180° C., n-octanol/water partition coefficient: 2.34) in isopropyl alcohol and adjusting the content of camphor to 0.99% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was about 40%. The occurrence of collapse (unevenness in collapse) of the pattern in the partial or local region was confirmed on the pattern-formed surface.

Comparative Example 2

In the present comparative example, a silicon substrate A was used as the substrate. A substrate treating liquid used as the substrate treating liquid was prepared by dissolving cyclohexanol (melting point: about 24° C., n-octanol/water partition coefficient: 1.25) in isopropyl alcohol and adjusting the content of camphor to 10% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 86.9%. The occurrence of collapse (unevenness in collapse) of the pattern in the partial or local region was confirmed on the pattern-formed surface.

Comparative Example 3

In the present comparative example, a silicon substrate A was used as the substrate. A substrate treating liquid used as the substrate treating liquid was prepared by dissolving cyclohexanol (melting point: about 24° C., n-octanol/water partition coefficient: 1.25) in isopropyl alcohol and adjusting the content of camphor to 20% by volume based on the total volume of the substrate treating liquid. Moreover, the rotation speed of the silicon substrate A when the substrate treating liquid is supplied onto the pattern-formed surface of the silicon substrate A was changed to 1,500 rpm. In the same manner as in Example 1 except for that, a drying treatment of the silicon substrate A was performed. By the same method as in Example 1, the effect of inhibiting pattern collapse was also evaluated. As a result, the collapse rate of the pattern was 87.4%. The occurrence of collapse (unevenness in collapse) of the pattern in the partial or local region was confirmed on the pattern-formed surface.

TABLE 10

| | Comparative Example 1 | Comparative Example 2 | Comparative Example 3 |
|---|---|---|---|
| Sublimable substance | Camphor | Cyclohexanol | |
| Solvent | Isopropyl alcohol | | |

TABLE 10-continued

| | Comparative Example 1 | Comparative Example 2 | Comparative Example 3 |
|---|---|---|---|
| Content of sublimable substance (% by volume) | 0.99 | 10 | 20 |
| Type of silicon substrate | A | A | A |
| Rotation speed in supplying step (rpm) | 1,500 | 1,500 | 1,500 |
| Pattern collapse rate (%) | about 40 | 86.9 | 87.4 |
| Presence or absence of unevenness in collapse of pattern | Present | Present | Present |
| Evaluation of treating | Failure | Failure | Failure |

(Results 4)

In the substrate treating liquid of Comparative Example 1 in which camphor was used as the sublimable substance and isopropyl alcohol was used as the solvent, it has been confirmed that many regions where the pattern is partially or locally collapsed on the pattern-formed surface are formed. The collapse rate of the pattern was also about 40%. In the substrate treating liquid of Comparative Examples 2 and 3 in which cyclohexanol was used as the sublimable substance and isopropyl alcohol was used as the solvent, it has been confirmed that many regions where the pattern is partially or locally collapsed on the pattern-formed surface are formed. The collapse rates of the patterns were 86.9% and 87.4%, respectively.

INDUSTRIAL APPLICABILITY

The present invention can be applied to dry technology for removing a liquid adhered to the surface of a substrate, and substrate processing technology in general for processing the surface of a substrate using the dry technology.

What is claimed is:

1. A substrate treating method for removing a liquid on a substrate having a pattern-formed surface, comprising:
- conducting a supplying step of supplying a substrate treating liquid to the pattern-formed surface,
- wherein the substrate treating liquid comprises cyclohexanone oxime as a sublimable substance and a solvent comprising at least alcohols.

2. The substrate treating method according to claim 1, wherein a concentration of the cyclohexanone oxime is in a range of 0.1% by volume or more and 10% by volume or less based on a total volume of the substrate treating liquid.

3. The substrate treating method according to claim 1, wherein the solvent is at least one selected from the group consisting of methyl alcohol, ethyl alcohol, isopropyl alcohol, n-butyl alcohol, tert-butyl alcohol and cyclohexanol.

4. The substrate treating method according to claim 1, wherein the cyclohexanone oxime is present in a state of being dissolved in the solvent, or the cyclohexanone oxime is present in the solvent in a molten state.

5. The substrate treating method according to claim 1, wherein isopropyl alcohol is adhered to the surface of the substrate.

6. The substrate treating method according to claim 1, comprising, subsequent to the supplying step, conducting a solidified film forming step of forming a solidified film on the surface of the substrate.

7. The substrate treating method according to claim 6, comprising, subsequent to the solidified film forming step, conducting a sublimation step of removing the solidified film from the surface of the substrate by sublimating the solidified film.

* * * * *